United States Patent
Vogel et al.

(10) Patent No.: US 9,254,336 B2
(45) Date of Patent: Feb. 9, 2016

(54) METHOD FOR ACTIVATION AND CONJUGATION OF BIOMOLECULES

(75) Inventors: Jens H. Vogel, El Cerrito, CA (US); Chi Shung Brian To, San Ramon, CA (US); Carolina Lucia Bianco, Kernen I. R. (DE)

(73) Assignee: BAYER HEALTHCARE LLC, Whippany, NJ (US)

( * ) Notice: Subject to any disclaimer, the term of this patent is extended or adjusted under 35 U.S.C. 154(b) by 0 days.

(21) Appl. No.: 13/580,102

(22) PCT Filed: Feb. 21, 2011

(86) PCT No.: PCT/US2011/025592
§ 371 (c)(1),
(2), (4) Date: Oct. 26, 2012

(87) PCT Pub. No.: WO2011/103531
PCT Pub. Date: Aug. 25, 2011

(65) Prior Publication Data
US 2013/0040362 A1   Feb. 14, 2013

Related U.S. Application Data

(60) Provisional application No. 61/306,513, filed on Feb. 21, 2010.

(51) Int. Cl.
*A61K 47/48* (2006.01)
*A61K 38/37* (2006.01)

(52) U.S. Cl.
CPC ........... *A61K 47/48215* (2013.01); *A61K 38/37* (2013.01)

(58) Field of Classification Search
None
See application file for complete search history.

(56) References Cited

U.S. PATENT DOCUMENTS

| 7,384,909 | B2 | 6/2008 | Thorpe et al. |
| 2007/0173634 | A1 | 7/2007 | Olsson et al. |
| 2008/0220448 | A1* | 9/2008 | Blincko et al. ................. 435/7.9 |
| 2009/0286955 | A1 | 11/2009 | Hatala et al. |

FOREIGN PATENT DOCUMENTS

| EP | 1578841 A2 | 9/2005 |
| WO | WO 2011017055 A2 * | 2/2011 |

OTHER PUBLICATIONS

Saxena, A., Tripathi, B.P., Kumar, M., and Shahi, V.K. "Membrane-based techniques for the separation and purification of proteins: An overview", Advances in Colloid asnd Interface Science 2009, vol. 145, pp. 1-22.*
Reddy, Ann. Pharmacother. 34:915-923, 2000.
Fung, et al., Polym. Prepr. 38:565-566, 1997.
Yowell, et al., Cancer Treat. Rev. 28 Suppl. A:3-6, 2002.
Muller, et al., Br. J. Haematol. 110:379-384, 2000.
Abshire, et al., Blood 96:1709-1715, 2000.
Safra, et al., Ann. Oncol. 11:1029-1033, 2000.
Judson, et al., Eur. J. Cancer 37:870-877, 2001.
Kim, et al., Biomaterials 23:2311-2317, 2002.
Wu, et al., Protein Expr. Purif. 48:24-27, 2006.
Piquet, et al., J. Chromatogr. 944:141-148, 2002.
Eto, et al., Int. J. Pharm. 354:3-8, 2008.
Hosseinkhani, et al., J. Control Release, 97:157-171, 2004.
Roberts, et al., Adv. Drug Deliv. Rev. 54:459-476, 2002.
Brocchini, et al., Adv. Drug Deliv. Rev. 60:3-12, 2008.
Schiavon, et al., Farmoco 55:264-269, 2000.
Lee, et al., Bioconjug. Chem. 18:1728-1734; 2007.

* cited by examiner

*Primary Examiner* — Renee Claytor
*Assistant Examiner* — Michelle F Paguio Frising
(74) *Attorney, Agent, or Firm* — Bayer Healthcare LLC

(57) ABSTRACT

The present invention is directed to a method for producing a biomolecule conjugate where the method is integrated into a single unit operation.

6 Claims, 7 Drawing Sheets

METHOD FOR ACTIVATION AND CONJUGATION OF BIOMOLECULES

FIELD OF THE INVENTION

The present invention is directed to a method for producing a biomolecule conjugate where the method is integrated into a single unit operation.

BACKGROUND OF THE INVENTION

With the advances in biotechnology, biopharmaceuticals have been developed to meet unmet medical needs. However, their short in-vivo half-life requires patients to take frequent and/or large doses of these biopharmaceuticals to achieve the target therapeutic or prophylactic goal. Long intravenous therapy or frequent injection could affect the patients' quality of life. Various polymers, such as polyethylene glycol (PEG), can be conjugated to a biomolecule (e.g., protein) to enhance the half-life and biologic activity of many biomolecules (Reddy, Ann. Pharmacother. 34:915-923, 2000). Other benefits of polymer conjugation include (a) improved product stability during the manufacturing process; (b) reduced renal clearance (Fung, et al., Polym. Prepr. 38:565-566, 1997); improved tumor trageting (Yowell, et al., Cancer Treat. Rev. 28 Suppl. A:3-6, 2002); reduced antigenicity and immunogenicity (Muller, et al., Br. J. Haematol. 110:379-384, 2000; Abshire, et al., Blood 96:1709-1715, 2000); and greater tolerability (Safra, et al., Ann. Oncol. 11:1029-1033, 2000; Judson, et al., Eur. J. Cancer 37:870-877, 2001). PEGylation has been applied to human growth factors (Kim, et al., Biomaterials 23:2311-2317, 2002; Wu, et al., Protein Expr. Purif. 48:24-27, 2006), growth hormone-releasing factor (Piquet, et al., J. Chromatogr. 944:141-148, 2002), adenovirus vector (Eto, et al., Int. J. Pharm. 354:3-8, 2008) and plasmid DNA (Hosseinkhani, et al., J. Control Release, 97:157-171, 2004). Due to the benefits of PEGylation, many conjugation reaction chemistry (Roberts, et al., Adv. Drug Deliv. Rev. 54:459-476, 2002) and polymer derivatives (European Patent No. 1578841) have been developed. As the application of biomolecule-polymer conjugation increases, it is necessary to develop simple, reproducible, and scalable unit operation to meet the manufacturing needs.

SUMMARY OF THE INVENTION

The present invention is directed to a method for producing a biomolecule conjugate comprising the steps of activating the biomolecule by contact with an activating agent; removing the activating agent; and conjugating the biomolecule by reacting the biomolecule with an activated polymer; wherein the steps of the method are integrated into a single unit operation. The method may further comprise the step of separating the biomolecule conjugate from unconjugated biomolecules. In one embodiment, the biomolecule conjugate is separated from unconjugated biomolecules by size exclusion chromatography or ion exchange chromatography.

In one embodiment, the single unit operation is an integrated tangential flow filtration system. In another embodiment, the activating agent is selected from a buffer exchange, pH adjustment, or a reducing agent. In a further embodiment, the reducing agent is dithiothreitol or tris 2-carboxyethyl phosphine. In other embodiments, the polymer is polyethylene glycol, and the biomolecule is selected from proteins, polysaccharides, and nucleic acids. In a further embodiment, the protein is selected from coagulation factors, antibodies, hormones, growth factors, and enzymes.

DESCRIPTION OF THE INVENTION

Figure 1:
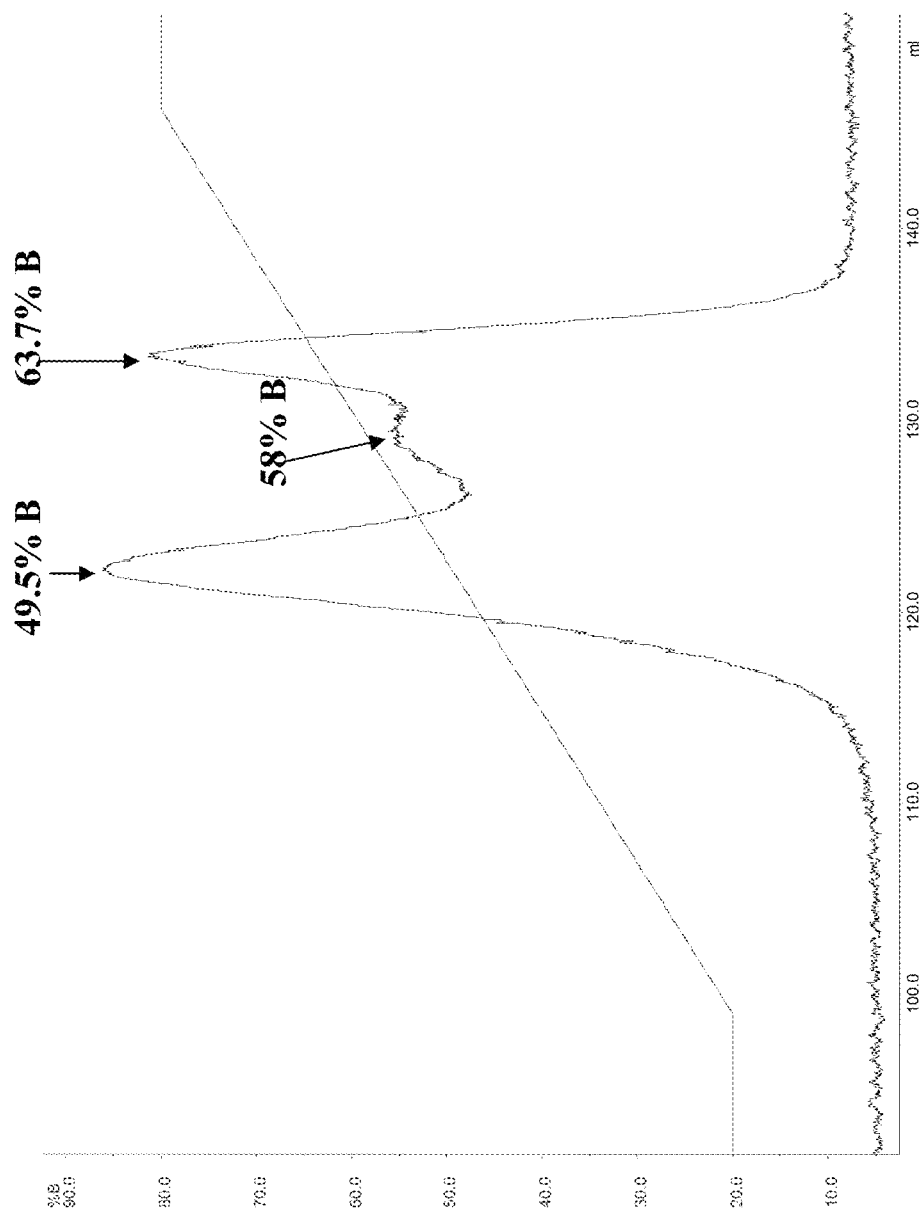
FIG. 1 Cation exchange chromatography elution profile of PEGylation control run.

It is to be understood that this invention is not limited to the particular device or parts described and as such may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural reference unless the context clearly dictates otherwise. Thus, for example, reference to "an agent" is a reference to one or more agents and includes equivalents thereof known to those skilled in the art, and so forth. Unless defined otherwise, all technical and scientific terms used herein have the same meaning as commonly understood to one of ordinary skill in the art to which this invention belongs.

Conjugation, such as PEGylation of biomolecule, may be random conjugation or site-specific conjugation. In both cases, the biomolecule is usually activated to allow efficient coupling of the polymer, such as PEG. In random PEGylation, PEG may be covalently conjugated to random activated amino acid residues. It usually results in a mixture of mono-PEGylated and multiple-PEGylated biomolecules. For site-specific PEGylation, a biomolecule may be genetically modified such that the PEG molecule can conjugate to a specific site on the surface of the biomolecules. This approach minimizes by-product formation and eases the burden of the subsequent purification step which separates the product from by-products.

The solvent exposed residues on the biomolecule may be activated by either adjusting the pH of the solution or by using reducing agents such as dithiothreitol (DTT) or tris 2-carboxyethyl phosphine (TCEP). After reduction, the PEG molecule may be attached to the activated residue via covalent linkage. If a reducing agent is used, it may be necessary to remove the reductant prior to the conjugation reaction. Size exclusion chromatography (SEC) is a common technique for lab-scale reductant removal.

Efficient state-of-the-art conjugation of biomolecules generally requires multiple unit operations, for example, activation through incubation/controlled mixing with a reducing agent, usually performed in a mixed vessel such as a stirred activation tank;

removal of the activation agent, typically by size exclusion chromatography or other chromatographic method;

conjugation through incubation/controlled mixing with the activated polymer (such as PEG), usually performed in a stirred conjugation tank; and separation of the conjugated biomolecule from unreacted molecules and byproducts by chromatography, such as ion exchange chromatography.

Such a process requires multiple systems and at a commercial scale, considerable space and manual handling/transfer between unit operations. In addition, SEC is difficult to implement in commercial scale manufacturing and requires set up as a stand-alone unit operation.

The method of the present invention integrates activation, removal of activation agent, and conjugation steps into one single unit operation by utilizing integrated tangential flow filtration for contacting/mixing and subsequent removal of reactants. While the target biomolecule is retained by utilizing membranes of suitable molecular weight cut-off, physicochemical conditions such as concentrations, pH, conductivity, and buffer species may be altered before, during, or after activation/conjugation. Adjustment of hydrodynamics in the system allows adjustment of optimal concentrations, and optionally the achievement of localized higher contacting concentrations at the membrane surface to further optimize the activation and conjugation process. This method is simple to operate, reproducible, scalable, and usable for commercial scale pharmaceutical production.

Examples of polymers that may be used in the method of the present invention include, but are not limited to, polyalkylene oxides such as polyethylene glycol, dextrans, colominic acids, or other carbohydrate based polymers, polymers of amino acids, biotin derivatives, polyvinyl alcohol (PVA), polycarboxylates, polyvinylpyrrolidone, polyethylene-co-maleic acid anhydride, polystyrene-co-malic acid anhydride, polyoxazoline, polyacryloylmorpholine, heparin, albumin, celluloses, hydrolysates of chitosan, glycogen, agaroses and derivatives thereof, guar gum, pullulan, inulin, xanthan gum, carrageenan, pectin, alginic acid hydrolysates, and any equivalents thereof. An example of a polyethylene glycol is methoxypolyethylene glycol (mPEG). Other useful polyalkylene glycol compounds are polypropylene glycols (PPG), polybutylene glycols (PBG), PEG-glycidyl ethers (Epox-PEG), PEG-oxycarbonylimidazole (CO1-PEG), branched polyethylene glycols, linear polyethylene glycols, forked polyethylene glycols and multi-armed or super branched polyethylene glycols (star-PEG).

Polyethylene glycol (PEG) includes any water-soluble poly(ethylene oxide). Typically, PEGs comprise the following structure "—(OCH$_2$CH$_2$)—" where (n) is 2 to 4000. As used herein, PEG also includes "—CH$_2$CH$_2$—O (CH$_2$CH$_2$O)—CH$_2$CH$_2$—" and (OCH$_2$CH$_2$)O—," depending upon whether or not the terminal oxygens have been displaced.

Polyethylene glycol also includes structures having various terminal or end capping groups, such as without limitation a hydroxyl or a C120 alkoxy group. Polyethylene glycol also means a polymer that contains a majority, that is to say, greater than 50%, of —OCH$_2$CH$_2$— repeating subunits. With respect to specific forms, PEG can take any number of a variety of molecular weights, as well as structures or geometries such as branched, linear, forked, and multifunctional.

Examples of biomolecules include, for example, any protein, polysaccharide, or nucleic acids. Proteins include, but are not limited to, coagulation factors, antibodies, hormones, growth factors, and enzymes.

The methods and materials described herein are intended to be representative examples of the invention, and it will be understood that the scope of the invention is not limited by the scope of the examples. Those skilled in the art will recognize that the invention may be practiced with variations on the disclosed methods and materials, and such variations are regarded as within the ambit of the invention.

EXAMPLES

In order that this invention may be better understood, the following examples are set forth. These examples are for the purpose of illustration only, and are not to be construed as limiting the scope of the invention in any manner. All publications mentioned herein are incorporated by reference in their entirety.

Example 1

PEGylation

In the control, tris 2-carboxyethyl phosphine (TCEP) stock solution was charged into 7.2 mL purified rFVIII solution (0.4 µM). After reduction, TCEP in the rFVIII solution was removed by SEC using a Superdex-75 column. Solid PEG was charged into the rFVIII solution to a final PEG concentration of 30 µM. The rFVIII was incubated with PEG for 13 hours at 2-8° C. At the end of the PEGylation incubation, the batch was diluted 3-fold and loaded onto a 4 mL cation exchange chromatography column. The rFVIII bound to the column was separated and eluted with a gradient.

In another run, 695 mL purified rFVIII solution (0.49 µM) was loaded into the retentate vessel of a tangential flow setup equipped with 50 cm$^2$ of 30 kDa regenerated cellulose tangential flow filtration (TFF) membrane. The rFVIII solution was first concentrated to 1.78 µM by permeating 500 mL permeate through the TFF membrane. After concentration, TCEP stock solution was charged to the concentrated rFVIII solution. Reduction incubation lasted for 30 minutes. Retentate cross flow rate was maintained 4 L/min/m$^2$ while the permeate was recycled back to the retentate vessel at 0.7 L/min/m$^2$. After reduction, TCEP in the retentate was removed by diafiltration against 5 volumes of PEGylation buffer. During diafiltration, retentate and permeate samples were taken after each diafilter volume to analyze for TCEP concentration. At the end of TCEP removal diafiltration, solid PEG was charged into the retentate vessel to achieve a final PEG concentration of 39 µM. The rFVIII was incubated with PEG for approximately 2 hours. During incubation, mixing was provided by recirculating the retentate through the TFF system at 4 L/min/m$^2$. At the end of PEGyation incubation, the retentate was harvested and diluted 4-fold. Part of the diluted retentate was loaded into a 5 mL cation exchange chromatography column. The rFVIII bound to the column was separated and eluted by gradient elution.

Fractions obtained from the gradient elution were analyzed by SDS-PAGE and analytical HPLC-SEC while the retentate and permeate samples were analyzed for TCEP by analytical HPLC assay.

The cation exchange chromatography elution profile of the control experiment is shown in FIG. 1. It consists of three elution peaks in which Peaks 1, 2, and 3 are eluted at 49.5%, 58%, and 63.7% of Buffer B, respectively.

Figure 2:
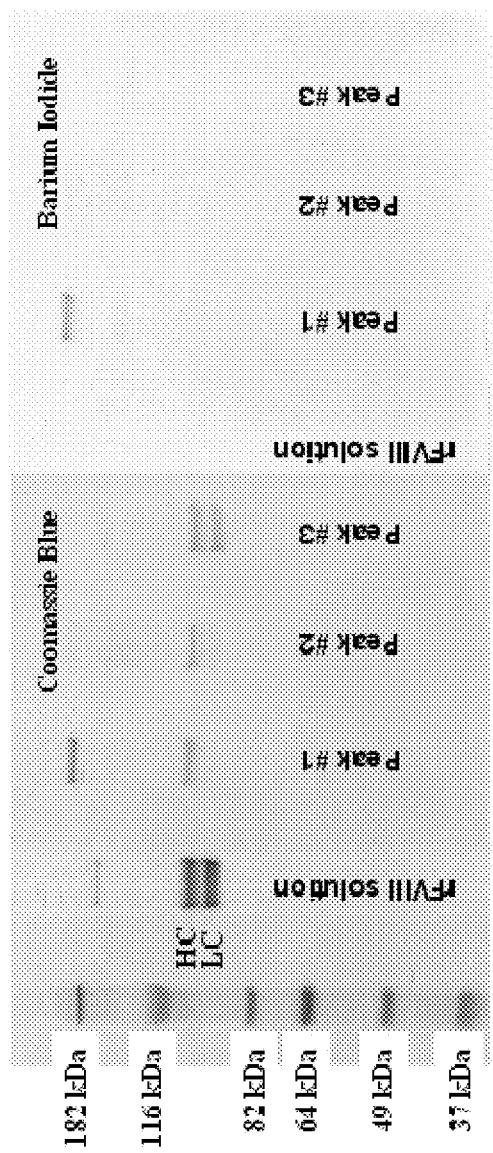
FIG. 2. SDS-PAGE of cation exchange chromatography elution peaks from PEGylation control run.

SDS-PAGE was used to characterize the elution peaks. Since barium iodide stain forms a complex with polyethylene glycol, the SDS-PAGE gel was first stained with barium iodide to confirm the conjugation of polyethylene glycol to rFVIII. After the image was taken, the gel was de-stained and then re-stained with Coomassie Blue. SDS-PAGE stained with Coomassie Blue shown in FIG. 2 indicates that rFVIII before PEGylation contains a heavy chain (HC) and a light chain (LC) which have molecular masses between 82 kDa and 116 kDa. After PEGylation, the light chain in the rFVIII in Peak 1 increases to higher than 182 kDa. The increase in molecular mass is due to the conjugation of polyethylene glycol to the light chain during PEGylation which is confirmed by the barium iodide stain. Peak 2 contains various protein species which are not PEGylated. Species collected in Peak 3 contains heavy chain and non-PEGylated light chain.

Figure 3:
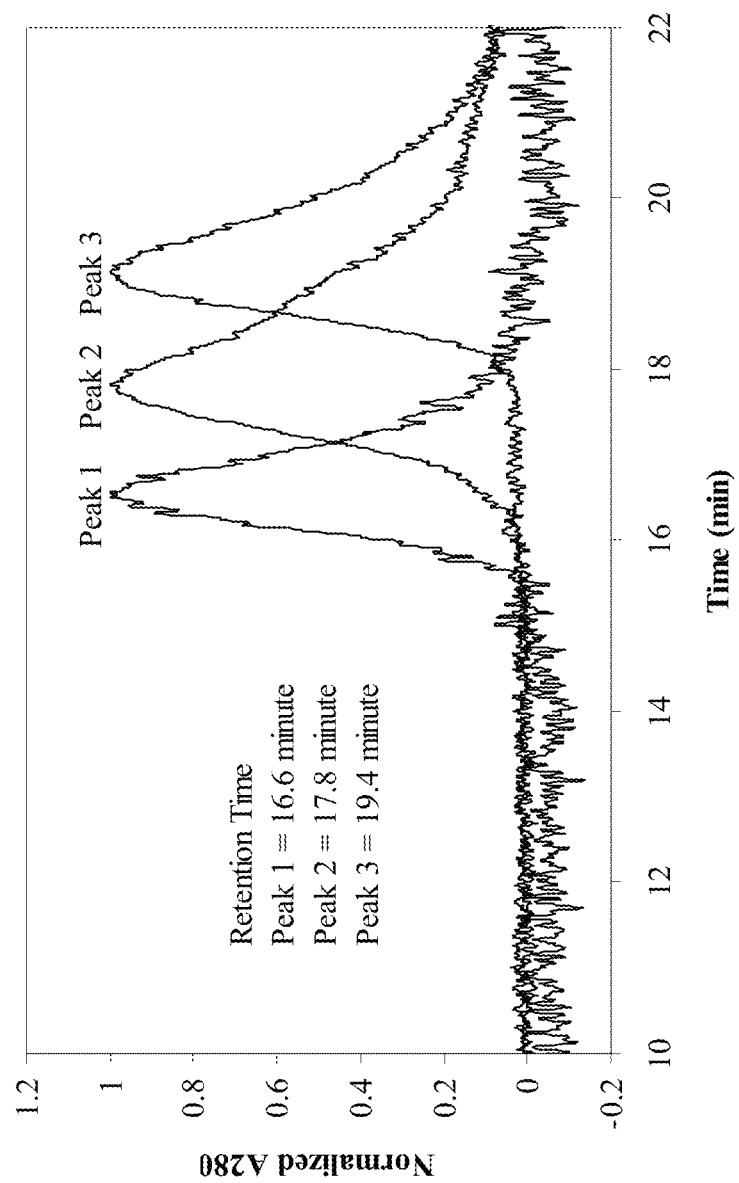
FIG. 3. Size exclusion chromatography of cation exchange chromatography elution peaks from PEGylation control.

A sample from each elution peak was also analyzed by SEC. FIG. 3 shows that the analytical SEC retention times of Peak 1 (PEGylated rFVIII), Peak 2, and Peak 3 (non-PEGylated rFVIII) are 16.6 minutes, 17.8 minutes, and 19.4 minutes, respectively. Since the retention time of the non-PEGylated rFVIII is 2.8 minutes longer than that of the PEGylated rFVIII, analytical SEC may be used as an orthogonal method to confirm the conjugation of PEG to the rFVIII molecule.

An additional step in the PEGylation process is the removal of reductant prior to the conjugation step. Table 1 shows that the retentate and permeate collected in the TFF mode PEGylation have similar TCEP concentrations at the end of each diafilter volume. TCEP in both retentate and permeate is reduced to below the assay detection limit after 4 diafilter volumes. This indicates diafiltration is effective in removing reductant.

TABLE 1

| Diafilter volume | Retentate TCEP (µM) | Permeate TCEP (µM) |
|---|---|---|
| 1 | 241.3 | 326.0 |
| 2 | 147.0 | 181.6 |
| 3 | 54.0 | 69.2 |
| 4 | 0 | 0 |
| 5 | 0 | 0 |

Figure 4:
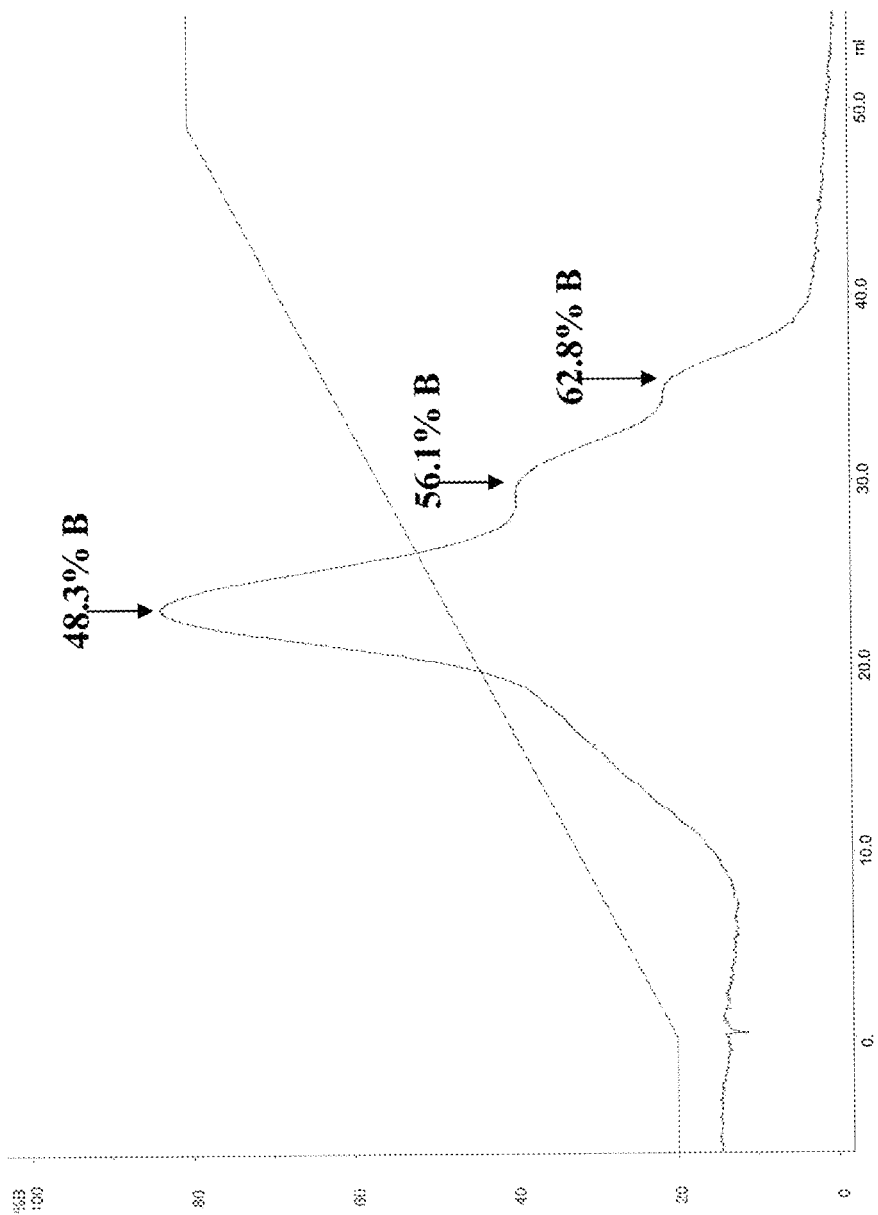
FIG. 4. Cation exchange chromatography elution profile of PEGylation performed in TFF mode.

The cation exchange chromatography elution profile of the material recovered from TFF mode PEGylation is shown in FIG. 4. Similar to FIG. 1, it also consists of three elution peaks in which Peaks 1, 2, and 3 are eluted at 48.3%, 56.1%, and 62.8% of Buffer B, respectively. The analytical HPLC-SEC retention time of Peaks 1 is 15.6 minutes compared to 18.5 minutes for Peak 3. The difference in retention time (2.9 minutes) between these two cation exchange chromatography elution peaks is consistent with that for the control arm. This demonstrates that the TFF mode PEGylation process may integrate the steps involved in biomolecule-polymer conjugation into a single TFF step.

Example 2

Consistency Study

Multiple lab-scale runs were performed to evaluate the consistency of the TFF mode PEGylation process. Volumes of 700-900 mL purified rFVIII solution were loaded into a Uniflux™ TFF system (GE Healthcare, Piscataway, N.J.) equipped with 50-100 cm² 30 kDa regenerated cellulose membrane (Millipore Corporation, Billerica, Mass.). The rFVIII solutions were concentrated to the target concentration. TCEP was charged into the retentate vessel to achieve an effective concentration of 250-450 µM and incubated for 30 minutes. After reduction, TCEP in the system was removed by diafiltration. PEG was charged to the reduced rFVIII to achieve an effective concentration of 13-26 µM and incubated for 10-15 hours. The retentate cross flow rate and permeate flow rate employed during concentration and diafiltration were 6-15 L/min/m² and 0.5-2 L/min/m², respectively. After PEGylation, the retentates were recovered from the TFF system, diluted, and loaded into a 56 mL cation exchange chromatography column. rFVIII bound to the column was separated and eluted by a gradient. Protein concentration was determined by analytical SEC-HPLC. Potency of samples was determined by chromogenic assay.

The membrane area used for the lab-scale runs is presented in Table. The initial concentrations of the rFVIII solutions used for the TFF runs range from 35 µg/mL to 55 µg/mL. The solutions were subsequently concentrated up to 10-fold prior to reduction and PEGylation.

TABLE 2

|  | Run 1 | Run 2 | Run 3 | Run 4 |
|---|---|---|---|---|
| TFF membrane area (cm²) | 50 | 50 | 100 | 100 |
| Initial rFVIII concentration (µg/mL) | 53.6 | 35.1 | 56.0 | 54.5 |
| Reduction rFVIII concentration (µg/mL) | 152 | 353 | 183 | 140 |
| rFVIII PEGylated (%) | 59% | 72% | 64% | 48% |

Figure 5:
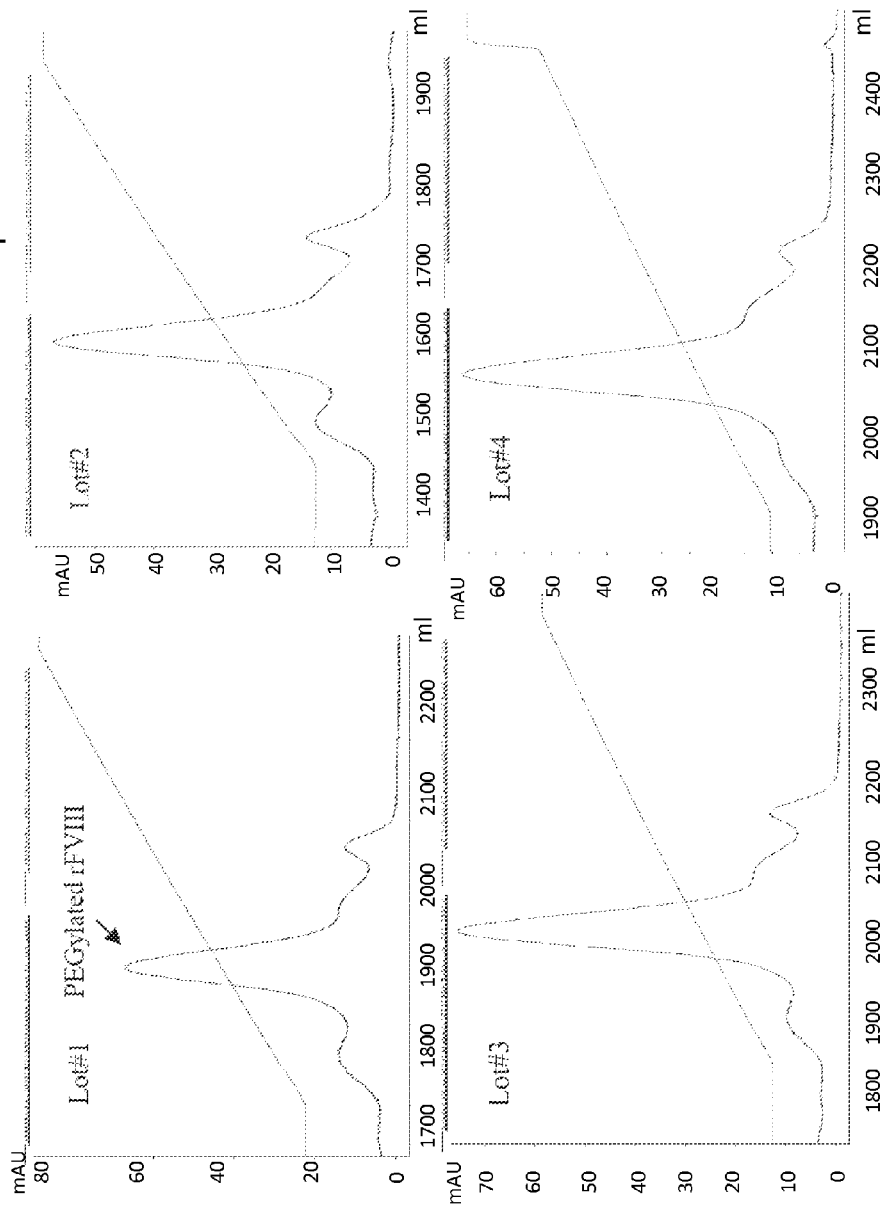
FIG. 5. Cation exchange chromatography elution profiles of lab-scale TFF runs.

The cation exchange chromatography elution profiles of the lab-scale TFF runs are presented in FIG. 5. These profiles are similar to that shown in FIG. 4 which contains PEGylated rFVIII, non-PEGylated rFVIII, and other rFVIII related species.

Figure 6:
FIG. 6. SEC profiles of PEGylated rFVIII produced by lab-scale TFF runs.

The analytical HPLC-SEC elution profiles shown in FIG. 6 indicate that the PEGylated rFVIII are mono-PEGylated. The HPLC-SEC retention time summarized in Table 3 shows that the PEGylated rFVIII is eluted 2.5-2.6 minutes earlier than the non-PEGylated rFVIII. This is consistent with those observed in Example 1.

TABLE 3

| Lab-scale Lot No. | rFVIII retention time (min.) | PEGylated rFVIII retention time (min.) |
|---|---|---|
| 1 | 16.6 | 14.1 |
| 2 | 16.7 | 14.1 |
| 3 | 16.6 | 14.1 |
| 4 | 16.6 | 14.1 |

The PEGylation efficiency of the TFF runs was calculated using the potency of the process intermediates. It ranges from 48-72% (TABLE) which is comparable to the PEGylation of other proteins (Brocchini, et al., Adv. Drug Deliv. Rev. 60:3-12, 2008; Schiavon, et al., Farmoco 55:264-269, 2000; Lee, et al., Bioconjug. Chem. 18:1728-1734; 2007). This example demonstrates that PEGylation in TFF mode is reproducible with PEGylation efficiency comparable to those reported in the literature.

Example 3

Pilot Scale TFF Mode PEGylation

Pilot scale TFF mode PEGylation runs were performed to demonstrate scalability of the process. In these runs, approximately 25 L rFVIII solution was transferred into a TFF skid equipped with 0.5 m² 30 kDa regenerated cellulose membrane. The rFVIII solution was concentrated and reduced by TCEP with an effective concentration of 600 µM. After reduction, TCEP was removed by diafiltration against the PEGylation buffer. PEG was charged to the reduced rFVIII to achieve an effective concentration of 40 µM. The cross flow rate and permeate flow rate employed during concentration and diafiltration were 7 L/min/m² and 1 L/min/m², respectively. At the end of PEGylation incubation, retentate was harvested, diluted, and loaded into a 4 L cation exchange chromatography column. Proteins bound to the column were separated and eluted by a gradient.

The PEGylated rFVIII was analyzed by analytical HPLC-SEC while the PEGylation efficiency was calculated based on the potency determined by the chromogenic assay.

Figure 7:
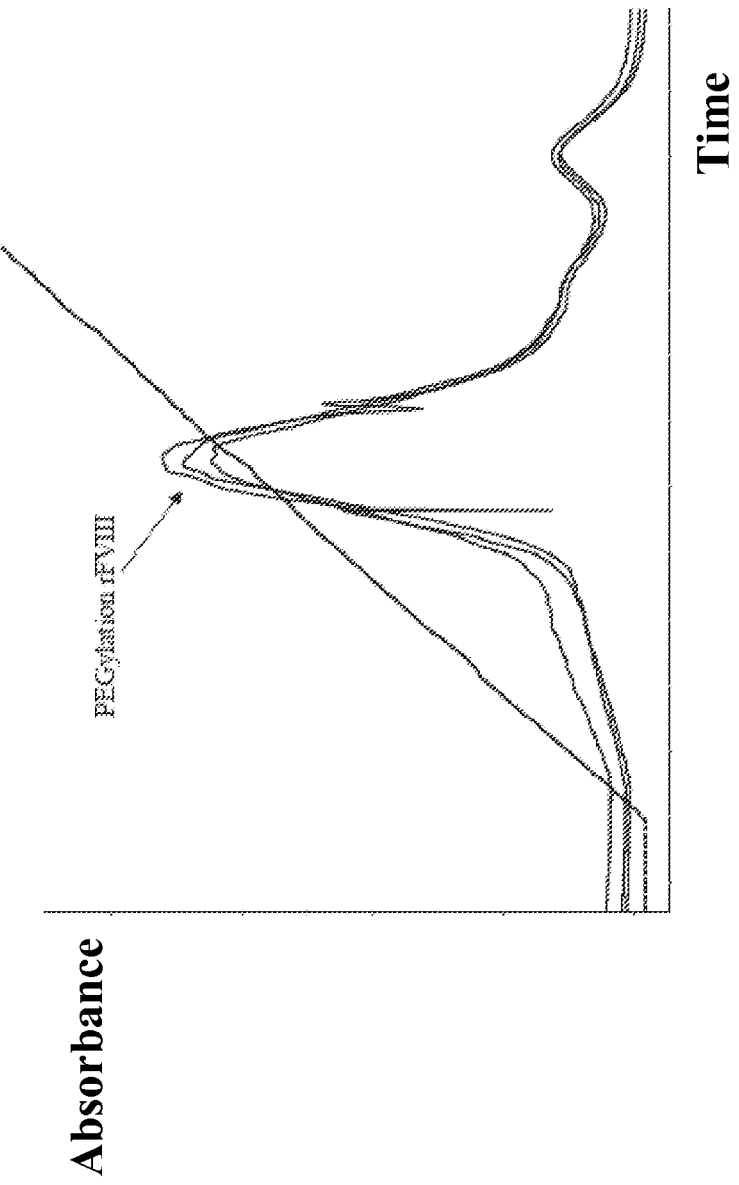
FIG. 7. Cation exchange chromatography elution profiles of pilot scale TFF runs.

The cation exchange chromatography elution profile of the pilot scale TFF mode PEGylation is shown in FIG. 7. Similar to those shown in previous examples, the elution profiles contain a PEGylated rFVIII peak and other rFVIII related species. The PEGylated rFVIII can be separated from other species by cation exchange chromatography with the appropriate gradient.

The retention times of the PEGylated and non-PEGylated rFVIII are summarized in Table 4. The difference in the retention time between these 2 rFVIII species is 3 minutes. The PEgylation efficiency ranged from 40-55%. These are also consistent with those shown in the previous examples. This example demonstrated that TFF mode PEGylation is scalable and consistent.

TABLE 4

| Lab-scale Lot No. | rFVIII retention time (min.) | PEGylated rFVIII retention time (min.) |
|---|---|---|
| 1 | 18.0 | 15.0 |
| 2 | 18.0 | 15.0 |
| 3 | 18.0 | 15.0 |

We claim:

1. A method for producing a biomolecule conjugate comprising the steps of activating the biomolecule by contact with an activating agent; removing the activating agent; and conjugating the biomolecule by reacting the biomolecule with an activated polymer; wherein the steps of the method are integrated into a single unit operation, wherein the single unit operation is an integrated tangential flow filtration system, wherein the polymer is polyethylene glycol and the biomolecule is a protein.

2. The method of claim 1, further comprising the step of separating the biomolecule conjugate from unconjugated biomolecules.

3. The method of claim 2, wherein the biomolecule conjugate is separated from unconjugated biomolecules by size exclusion chromatography or ion exchange chromatography.

4. The method of claim 1, wherein the activating agent is selected from a buffer exchange, pH adjustment, or a reducing agent.

5. The method of claim 4, wherein the reducing agent is dithiothreitol or tris 2-carboxyethyl phosphine.

6. The method of claim 1, wherein the protein is selected from coagulation factors, antibodies, hormones, growth factors, and enzymes.

* * * * *